United States Patent [19]

Igaue et al.

[11] Patent Number: 5,167,653

[45] Date of Patent: Dec. 1, 1992

[54] DISPOSABLE GARMENTS

[75] Inventors: Takamitsu Igaue; Hirotomo Mukai, both of Kawanoe; Michiyo Matsushita, Iyomishima, all of Japan

[73] Assignee: Uni-Charm Corporation, Ehime, Japan

[21] Appl. No.: 806,234

[22] Filed: Dec. 12, 1991

[30] Foreign Application Priority Data

Dec. 18, 1990 [JP] Japan .................................. 2-411432

[51] Int. Cl.$^5$ ............................................. A61F 13/15
[52] U.S. Cl. .................................................. 604/385.2
[58] Field of Search ................... 604/358, 385.1, 385.2

[56] References Cited

U.S. PATENT DOCUMENTS

| | | | |
|---|---|---|---|
| 4,695,278 | 9/1987 | Lawson | 604/385.2 |
| 4,808,177 | 2/1989 | DesMarais | 604/385.1 |
| 4,816,025 | 3/1989 | Foreman | 604/385.2 |
| 4,904,251 | 2/1990 | Igaue et al. | 604/385.2 |
| 5,021,051 | 6/1991 | Hiuke | 604/385.2 |

FOREIGN PATENT DOCUMENTS

| | | |
|---|---|---|
| 0219326 | 4/1987 | European Pat. Off. . |
| 0346477 | 12/1989 | European Pat. Off. . |
| 2161059 | 1/1986 | United Kingdom . |
| 2193625 | 2/1988 | United Kingdom . |
| 2216393 | 10/1989 | United Kingdom . |
| 8902228 | 3/1989 | World Int. Prop. O. ........ 604/385.1 |

*Primary Examiner*—Ronald Frinks
*Assistant Examiner*—Mary Beth O. Jones
*Attorney, Agent, or Firm*—Fred Philpitt

[57] ABSTRACT

The present invention relates to a disposable garment for catching body fluids or excretions and particularly to a garment provided with a plurality of flaps extending longitudinally side-by-side along laterally opposite sides of the garment and normally biased by their own elastic shrinking potential to turn up.

6 Claims, 4 Drawing Sheets

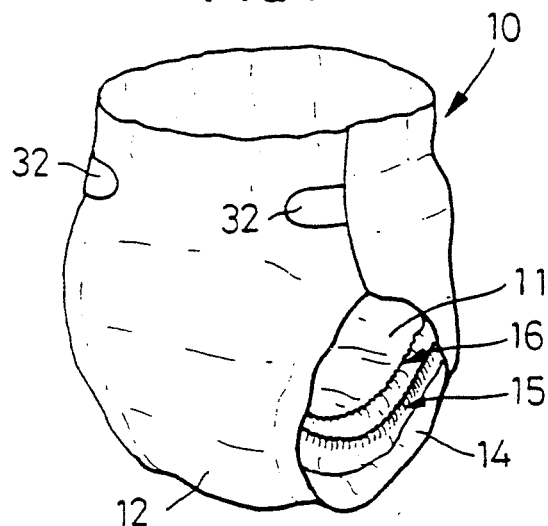
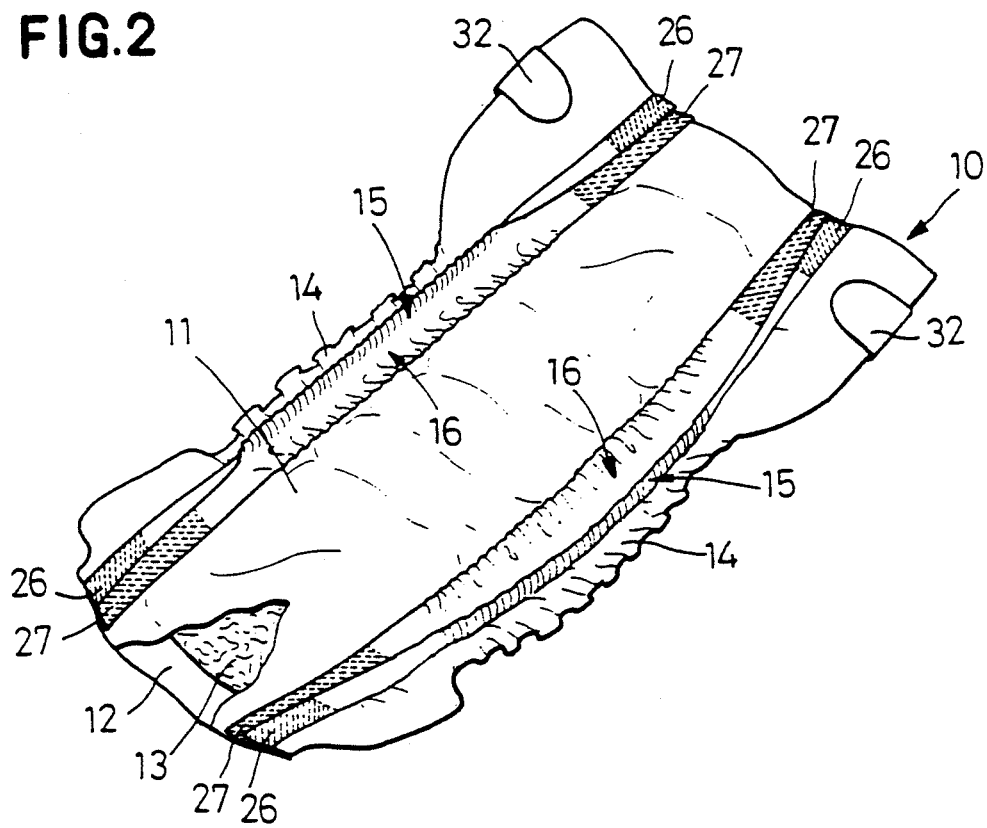

DISPOSABLE GARMENTS

BACKGROUND OF THE INVENTION

The present invention relates to disposable garments used to catch body fluids or excretions and more particularly to such disposable garments provided with a plurality of flaps longitudinally extending side by side along laterally opposite sides of the garments and normally biased by their own elastic shrinking potential to turn up.

U.S. Pat. No. 4,695,278 (referred to hereinafter as the first prior art) discloses garments such as disposable diapers comprising a liquid-permeable inner sheet, a liquid-impermeable outer sheet, a liquid-absorptive core sandwiched between these sheet, a pair of base flaps (i.e., gasket cuffs) extending outward from laterally opposite side edges of said core and provided with elastic members, respectively, and a second pair of flaps (i.e., barrier cuffs) having root edges on areas of the respective base flaps extending inwardly from the respective elastic members and normally biased by elastic members mounted along free edges of the respective second flaps to turn up along said root edges. Said base flaps are pressed against respective thighs of the wearer. Said second pair of flaps are fixed at longitudinally opposite end with said ends being collapsed inward and with intermediate portions being biased by their own elastic shrinking potential to turn up and thereby free edges of these intermediate portions being pressed against roots of the wearer's thighs.

U.S. Pat. No. 4,904,251 (referred to hereinafter as the second prior art) discloses disposable diapers comprising a liquid-permeable inner sheet, a liquid-impermeable outer sheet, a liquid-absorptive core sandwiched between these sheets, a pair of base flaps extending outward from laterally opposite side edges of said core, and a second pair of flaps having root edges on the upper surfaces of the respective base flaps and normally biased by elastic members mounted along their free edges to turn up along the respective root edges. Said second pair of flaps are fixed at longitudinally opposite ends with said ends being collapsed outward and with intermediate portions being biased by their own elastic shrinking potential to turn up and thereby free edges of these intermediate portions being pressed against roots of the wearer's thighs.

Initially, said first prior art will be considered.

Said base flaps have a rather planer configuration and are curved under the effect of their own elastic shrinking potential but insufficiently to fit around the thighs and thereby to prevent excretions from leaking out, as has usually been the case with the flaps of the conventional disposable diapers.

In order that the pockets defined by said second pair of flaps adapted to be pressed against the thigh roots of the wearer can adequately opened and reliably catch excretions, it is essential that the free edges of the respective second flaps should be always stabilized against the thighs' roots of the wearer. However, the first prior art discloses neither width dimensioning nor stiffness adjustment for each second flap required to achieve such ideal fitness.

The free edges of the second flaps must be always stabilized against the roots of the wearer's thighs as has been mentioned above, but the pressure at which the second flaps are pressed against the thighs' roots are too high so that wearing of this prior art for a relatively long period will result in a pressure mark on the wearer's skin and pain.

Said second prior art will be considered.

Said base flaps have no elastic shrinkability and therefore can not be elastically pressed against the wearer's thighs for positive prevention of excretions leakage. Certainly, the second pair of flaps have such function, but, in view of the position at which each second flap is pressed against the wearer's body, these second flaps correspond to the base flaps of the first prior art. In other words, the second prior art has no members corresponding to the second flaps of the first prior art.

Accordingly, it is a principal object of the present invention to provide disposable garments so improved to solve the above-mentioned problem encountered by the first and second prior arts by providing members corresponding to the second flaps of the first and second prior arts and setting tensile stress, width and stiffness of the members corresponding to the second flaps of the first prior art to optimized levels.

ASPECTS OF THE INVENTION

The object set forth above is achieved, in accordance with the present invention, by a garment comprising a liquid-absorptive core, a first pair of flaps extending along laterally opposite sides of the article and a second pair of flaps extending inside the respective first flaps, wherein both the first and second pairs of flaps have elastic shrinking potential by which these flaps are biased to turn up. In addition, a tensile stress of the second flaps is adjusted to be lower than a tensile stress of the first flaps, a width of each second flap is dimensioned to be larger than a width of each first flap, and stiffness of the second flaps is adjusted to be lower than a stiffness of the first flaps.

Preferably, the first and second pairs of flaps are branched from associated base flaps extending outward from laterally opposite side edges of the liquid-absorptive core, respectively. In this embodiment, the first and second pairs of flaps may be provided independently or continuously.

When the garment of the invention having the arrangement as has been described above is put on the wearer's body, the free edges of the respective first flaps are pressed relatively tight against the wearer's thighs and the free edges of the second flaps are pressed rather loosely around the wearer's thigh roots. During movement of the wearer's legs, the free edges of the first flaps slidably move on the skin of the wearer's thighs and the free edges of the second flaps remain substantially fixed around the thigh roots.

According to the invention, the tensile stress of each second flap is lower than that of each first flap so that, even if the second flap continues to be pressed against the wearer's skin for a relatively long period, the area of the skin against which the second flap has been pressed is free from any pressure mark or pain.

The other important feature of this invention such that the width (or the height) of each second flap as measure from the root edge to the free edge of this second flap is dimensioned to be larger than that of each first flap as measured from the root edge to the free edge of this first flap and the stiffness of each second flap is adjusted to be lower than that of each first flap is effective to absorb or attenuate any movement of the diaper, the body or the thighs of the wearer instead of transferring such movement to the free edge of each second flap which is held against the thigh around the root thereof. Accordingly, the free edge of each second flap is stabilized against the thigh root and thus the pocket defined by the second flap is kept open so that liquid or solid excretions can be reliably received by this pocket. Any quantity of excretions which was forced, no matter what the cause is, beyond the second flap is effectively prevented by the associated first flap from further flowing out.

According to the invention, furthermore, there is provided on each base flap the absorbent layer between the pair of first and second flaps associated with this base flap so that any quantity of excretions sometimes present between these first and second flaps can be absorbed by this absorbent layer for further reliable prevention of said leakage.

BRIEF DESCRIPTION OF THE DRAWINGS

FIG. 1 is a perspective view showing an individual disposable diaper, in assembled condition, as one of embodiments of garment constructed in accordance with the teachings of the present invention;

FIG. 2 is a perspective view showing said diaper in developed condition;

PREFERRED EMBODIMENTS OF THE INVENTION

Several embodiments of disposable diaper will be described as embodiments of a garment constructed in accordance with the teachings of the present invention with reference to the attached drawings.

Figure 3:
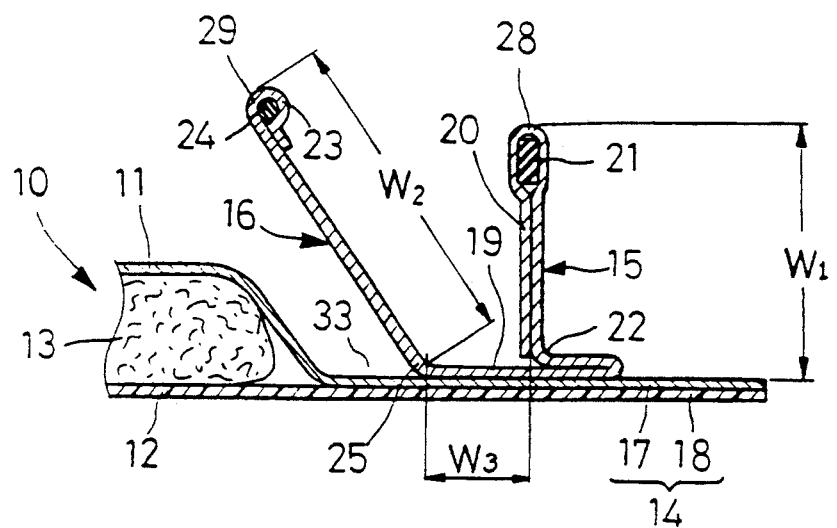
FIG. 3 is a sectional view showing an important part of said diaper.

Referring to FIGS. 1 through 3, a diaper 10 comprises a liquid-permeable inner sheet 11, a liquid-impermeable outer sheet 12, a liquid-absorptive core 13, a pair of laterally opposite base flaps 14, a first pair of laterally opposite flaps 15 and a second pair of laterally opposite flaps 16. The base flaps 14 extend outward from opposite outer edges of the core 13, respectively, and each comprises portions 17, 18 of the inner and outer sheets bonded together by adhesive or welding (inclusive of ultrasonic welding).

Both the first flaps 15 and the second flaps 16 are formed by an air-permeable but liquid-resistant sheets 19 bonded substantially over central zones to the upper surfaces of the respective base flaps 14 by adhesive or welding (inclusive of ultrasonic welding). Each of these first flaps 15 contains an elastic member 21 within a sleeve-like free edge 20 defined by a portion of the sheet 19 and said elastic member 21 has been mounted in its longitudinally stretched condition so that an elastic shrinkability of said elastic member 21 biases this first flaps 15 to turn up along its root edge 22 along which said first flap 15 is branched away from the associated base flaps 14. Similarly, each of the second flaps 16 contains an elastic member 24 within a sleeve-like free edge 23 defined by another portion of the sheet 19 and said elastic member 24 has been mounted in its longitudinally stretched condition so that an elastic shrinkability biases this second flap 16 to turn up along its root edge 25 which is inwardly spaced from said root edge 22 by an appropriate distance and along which said second flap 16 is branched away from the associated base flap 14. Each of the first flaps 15 is bonded at longitudinally opposite ends 26 onto the associated base flap 14 by adhesive or welding (inclusive of ultrasonic welding) with a longitudinally intermediate portion of this flap 15 maintained as it turns up and with said longitudinally opposite ends 26 collapsed inward. However, it should be understood that the first flap 15 may be bonded onto the associated base flap 14 in an alternative manner, i.e., with said longitudinally intermediate portion maintained as it turns up but with said longitudinally opposite ends 26 collapsed outward. Similarly, each of the second flaps 16 is bonded at longitudinally opposite ends 27 onto the associated base flap 14 and the core 13 by adhesive or welding (inclusive of ultrasonic welding) with a longitudinally intermediate portion maintained as it turns up and with said longitudinally opposite ends 27 collapsed inward so as to define a relatively deep pocket 33. Although both the first and second flaps 15, 16 having the intermediate portions between said longitudinally opposite ends 26, 27, respectively, which are normally biased to turn up, these intermediate portions also will be collapsed inward as these flaps 15, 16 are longitudinally stretched substantially to predetermined stretch limits. Obviously, when the first flap 15 is bonded at the longitudinally opposite ends 26 onto the associated base flap 14 in said alternative manner, i.e., with the intermediate portion maintained as it turns up and with said longitudinally opposite ends 26 collapsed outward, said intermediate portion will be collapsed outward as this flap 15 is stretched in its longitudinal direction substantially to the predetermined stretch limit.

A tensile stress of the second flaps 16 is adjusted to be lower than a tensile stress of the first flap 15 so that an area of the wearer's skin against which the second flap 16 has been pressed under shrinking potential thereof be free from any pressure mark or pain even after said second flap 16 has been pressed against the wearer's skin for a relatively long period. A tensile stress of the elastic member 21 is typically adjusted to a value from 100 g to 300 g. A width (or height) $W_2$ of the second flap 16 as measured from the root edge 25 to the free edge 29 is dimensioned to be larger than a width (or height) $W_1$ of the first flap 15 as measured from the root edge 22 to the free edge 28 and a stiffness of the second flap 16 is adjusted to be lower than a stiffness of the first flap 15 so that any movement of the diaper 10, the body or the thighs of the wearer be absorbed or attenuated instead of being transferred to the free edge 29 of the second flap 16 which is held against the thigh around a root thereof. For example, the width $W_1$ of the first flap 15 may be 20 mm to 35 mm, the width $W_2$ of the second flap 16 may be 30 mm to 100 mm, and longitudinal and transverse dimensions of the second flap 16 as measured in accordance with the Japanese-Industrial-Standard-P8143 may be less than 100 mm and less than 60 mm, respectively. The corresponding dimensions of the first flap 15 may be substantially equal to those of the side flap in the typical disposable diaper of prior art. Preferably, a width $W_3$ as measured between the root edges 22, 25 should not be larger than the width $W_1$ of the first flap 15. The root edge 25 may be positioned adjacent to or in contact with the associated outer side edge of the core 13.

Figure 4:
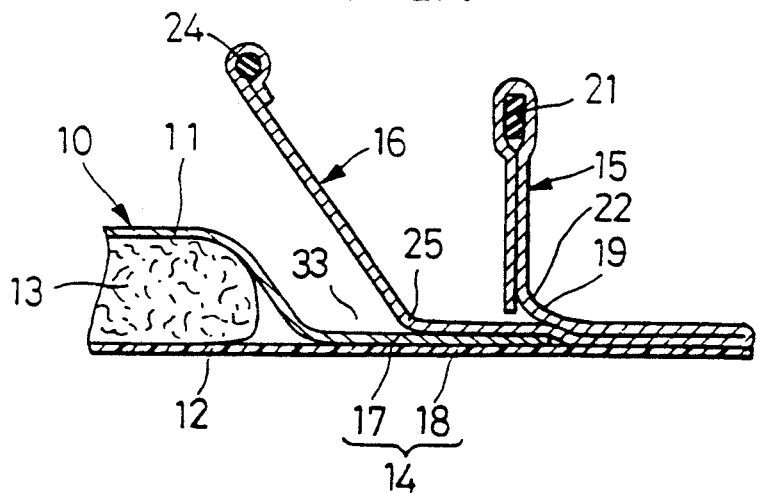
FIG. 4 is a view similar to FIG. 3 but showing another embodiment.

In an alternative embodiment shown by FIG. 4, each of the base flaps 14 comprises the portion 17 of the inner sheet and the portion 18 of the outer sheet having a width larger than that of said portion 17. In other words, the base flap 14 is so formed that said portion 18 extends outward from the outer side edge of said portion 17. The sheet 19 is partially bonded onto such extension of said portion 18 along which said portion 17 does not lie on the top of said portion 17 and thereby forms the first and second flaps 15, 16. This embodiment is particularly advantageous in that a material saving is achieved for the inner sheet 11 since the inner sheet 11 may have a width narrower than that of the outer sheet 12 and any leakage of body fluids which might otherwise occur beyond the outer side edges of the respective base flaps 14 can be avoided even if said body fluids permeate and diffuse into the liquid-permeable portion 17 of the inner sheet since the liquid-resistant sheet 19 forming the first and second flaps 15, 16 is bonded to the portion 18 of the liquid-impermeable outer sheet without said liquid-permeable inner sheet interposed therebetween.

Figure 5:
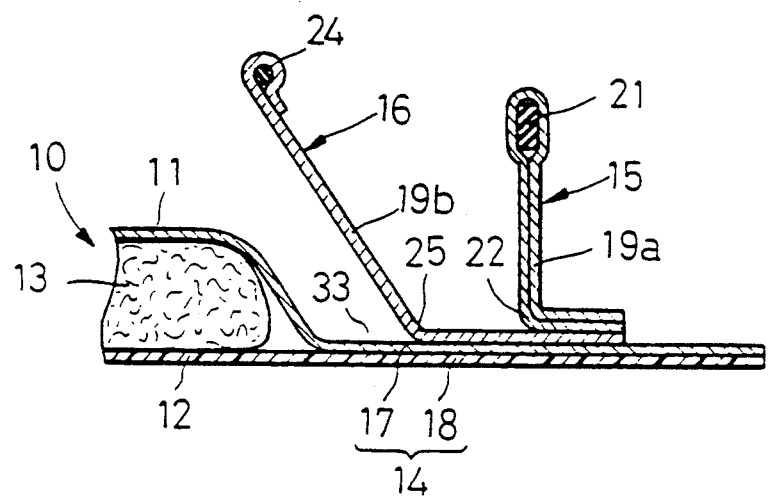
FIGS. 5 and 6 are views similar to FIGS. 3 and 4, respectively, showing further embodiments.
Figure 6:
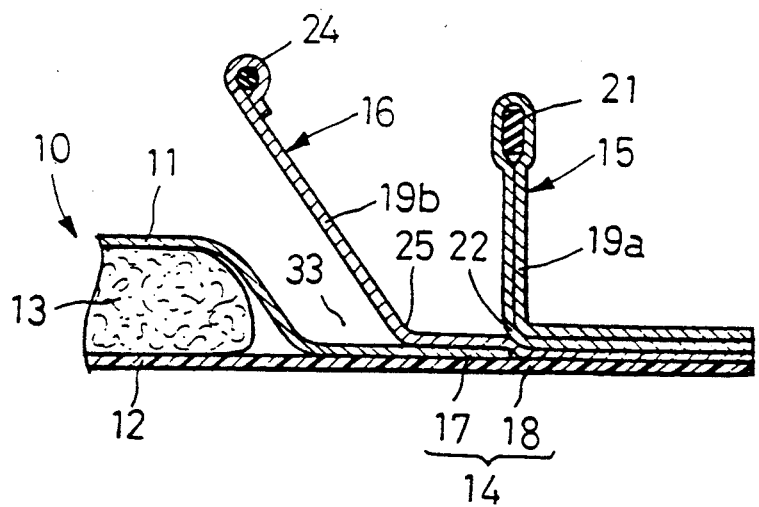

The first and second flaps are formed, in still another embodiment shown by FIGS. 5 and 6, from different sheets 19a, 19b, respectively. A water pressure resistance (liquid-impermeability) of the first flap 15 is adjusted to a value higher than that of the second flap 16. Except such feature, the arrangement of the first and second flaps 15, 16 and the base flaps 14 in this embodiment is substantially the same as in the embodiment shown by FIGS. 3 and 4.

Figure 7:
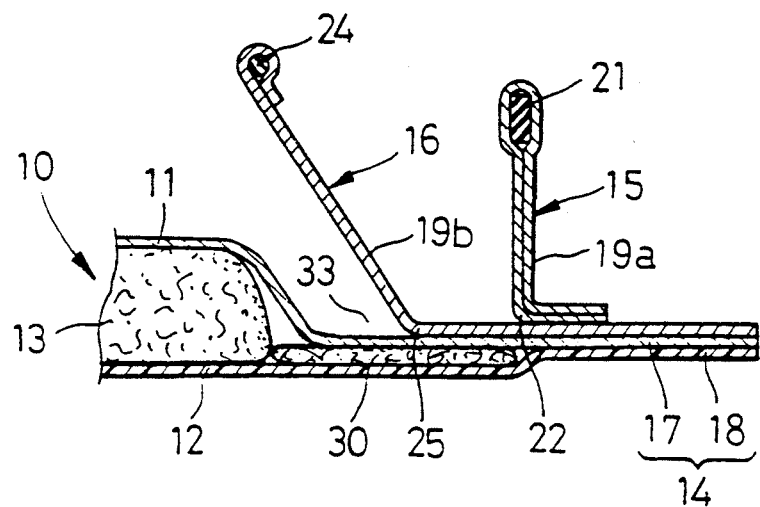
FIGS. 7 and 8 are views similar to FIGS. 3 and 4, respectively, showing still other embodiments both including absorbent layers placed on the base flaps.
Figure 8:
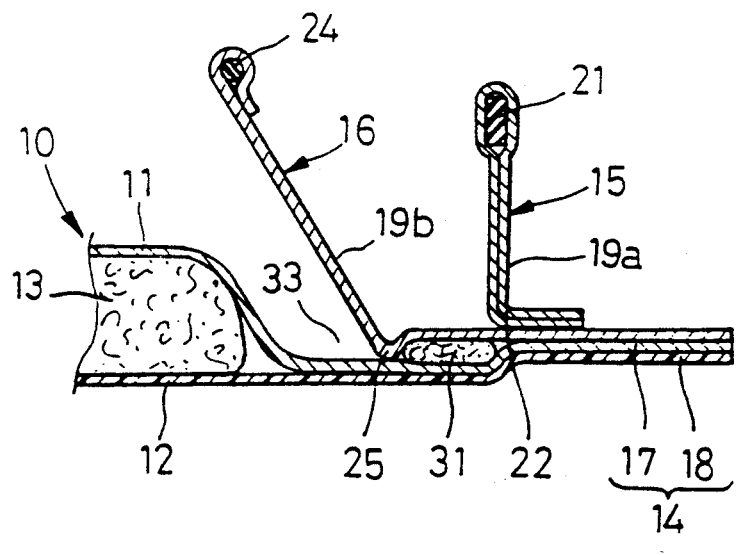

In an embodiment shown by FIG. 7, there is interposed a relatively thin, highly flexible absorbent layer 30 between the portions 17, 18 of the inner and outer sheets, respectively, so as to extend between the outer side edge of the core 13 and the root edge 22 of the associated first flap 15. In an embodiment shown by FIG. 8, there is interposed a relatively thin, highly flexible absorbent layer 31 between the portion 17 of the inner sheet and the sheet 19b so as to extend between the root edges 22, 25 of the first and second flaps 15, 16. These embodiments are adapted to provide a liquid absorptivity at least between the root edges 22, 25 so that any quantity of body fluids which might stay between the first and second flaps 15, 16, even if such stay is temporary, can be absorbed by the absorbent layers 30, 31, respectively.

As will be apparent from FIGS. 1 and 2, tape fasteners 32 applied with pressure-sensitive adhesive are attached to the respective base flaps 14 on the rear side of the diaper 10. The diaper 10 can be assembled on the body of the wearer by fastening free ends of the respective tape fasteners 32 onto the outer sheet 12.

The inner sheet 11 is formed from material such as fibrous nonwoven fabric or porous plastic film and the outer sheet 12 is formed from material such as plastic film or laminate sheet of said film and nonwoven fabric. It should be understood that such laminate sheet is used with the nonwoven fabric facing outward. The plastic film which is suitable as material for the outer sheet 12 is preferable air-impermeable. the core 13 comprises a mat-like body formed from fluff pulp mixed or not mixed with superabsorbent polymer powder and covered with liquid-permeable sheet at least over top and bottom sides. In view of the material from which the core 13 is formed, the core 13 is semi-rigid. It will be obviously understood that the core 13 is rather firmly bonded to the inner sheet 11 and/or the outer sheet 12 with adhesive. The elastic members 21, 24 respectively comprise material such as thread- or tape-like rubber, tape-like plastic foam or plastic film presenting elastic stretchability under heat treatment. The first and second flaps 15, 16 are formed from water-repellent nonwoven fabric. However, it is not always essential that the second flaps 16 should be formed from liquid-resistant material so long as the second flaps 16 can properly function to hold back any possible leakage of solid excretion since the second flaps 16 have been surfactant-treated particularly over their inner surfaces and thereby obtained hydrophilicity. The absorbent layers 30, 31 comprise narrow strips formed from fluff pulp mixed or not mixed with superabsorbent polymer powder.

When the diaper 10 having the construction as has been described above is put on the wearer's body, the first and second flaps 15, 16 turn up (i.e., toward the wearer's body) along the respective root edges 22, 25 under the elastic shrinkage of the respective elastic members 21, 24 wrapped by the respective free edges 28, 29. However, both the first and second flaps 15, 16 have their root edges 22, 25 intersecting the associated base flaps 14 or bend relative to the associated base flaps 14 so as to form inverted T-shaped cross-sections and, in consequence, said elastic shrinkage of the respective elastic members 21, 24 is substantially prevented from being transferred through the respective root edges 22, 25 to the outer sides of the respective base flaps 14. In other words, presence of the root edges 22, 25 minimizes a phenomenon that the elastic shrinkage of the elastic members 21, 24 might be transferred directly to the outer sides of the respective base flaps 14, resulting in that said outer sides might be creased with wrinkles.

What is claimed is:

1. A disposable garment comprising a liquid-permeable inner sheet (11) joined to a liquid-impermeable outer sheet (12) with a liquid absorptive core (13) interposed therebetween, a pair of first flaps (15), a pair of second flaps (16), each of said pairs (15, 16) extending longitudinally with respect to said liquid-absorptive core (13) along laterally opposite sides thereof, said garment being further characterized by the fact that:
   (1) said pair of first flaps (15) containing elastic (21) and having their root edges (22) located on laterally opposite sides of said core (13) and being mounted so that the first flaps (15) will turn upwardly under their own elastic shrinking potential,
   (2) said second pair of second flaps (16) having their root edges (25) located at a spaced distance (W3) inwardly from said root edges (22) of said pair of first flaps (15) and containing elastic so that the second flaps (16) after mounting will also turn upwardly under their own elastic shrinking potential,
   (3) each second flap (16) having a tensile stress lower than the tensile strength of each first flap (15),
   (4) the width of each second flap (16) as measured from its root edge to its free edge being greater than the width of each first flap (15) as measured from its root edge to its free edge, and
   (5) the stiffness of each flap (16) being lower than the stiffness of each first flap (15).

2. A disposable garment according to claim 1 wherein a liquid absorptive layer (30, 31) is included in the spaced distance (W3) between the root edge (22) of said first flap (15) and the root edge (25) of said second flap (16).

3. A disposable garment as recited in claim 1 wherein said first and second pairs of flaps (15, 16) are fastened at their longitudinally opposite ends (26, 27) with said first pair of flaps (15) being collapsed inward or outward and said second pair of flaps (16) being collapsed inward.

4. A disposable garment comprising a liquid-permeable inner sheet (11) joined to a liquid-impermeable outer sheet (12) with a liquid absorptive core (13) interposed therebetween, laterally extending base flaps (14), a pair of first flaps (15), a pair of second flaps (16), each of said pairs (15, 16) extending longitudinally with respect to said liquid-absorptive core (13) along laterally opposite sides thereof and being located inwardly with respect to the outer lateral edges of said bases flaps (14), said garment being further characterized by the fact that:

(1) said pair of first flaps (15) containing elastic (21) and having their root edges (22) located on laterally opposite sides of said core (13) and being mounted so that the first flaps (15) will turn upwardly under their own elastic shrinking potential, (2) said pair of second flaps (16) having their root edges (25) located at a spaced distance (W3) inwardly from said root edges (22) of said pair of first flaps (15) and containing elastic so that the second flaps (16) after mounting will also turn upwardly under their own elastic shrinking potential, (3) each second flap (16) having a tensile stress lower than the tensile strength of each first flap (15), (4) the width of each second flap (16) as measured from its root edge to its free edge being greater than the width of each first flap (15) as measured from its root edge to its free edge, and (5) the stiffness of each second flap (16) being lower than the stiffness of each first flap (15).

5. A disposable garment according to claim 4 wherein a liquid absorptive layer (30, 31) is included in the spaced distance (W3) between the root edge (22) of said first flap (15) and the root edge (25) of said second flap (16).

6. A disposable garment as recited in claim 4 wherein said first and second pairs of flaps (15, 16) are fastened at their longitudinally opposite ends (26, 27) with said first pair of flaps (15) being collapsed inward or outward and said second pair of flaps (16) being collapsed inward.

* * * * *